United States Patent [19]

Lormeau et al.

[11] 4,115,551
[45] Sep. 19, 1978

[54] COMPOUNDS OF THE PLASMINOGEN TYPE AND METHOD FOR OBTAINING SUCH COMPOUNDS FROM PLACENTAL PULPS

[75] Inventors: Jean-Claude Lormeau, Maromme-la-Maine; Jean Goulay, Oissel; Edmond Vairel, Paris, all of France

[73] Assignee: Choay S.A., Paris, France

[21] Appl. No.: 533,631

[22] Filed: Dec. 17, 1974

[30] Foreign Application Priority Data

Dec. 18, 1973 [FR] France ............................. 73 45289

[51] Int. Cl.$^2$ ........................................... A61K 35/50
[52] U.S. Cl. ................................................. 424/105
[58] Field of Search ........................................ 424/105

[56] References Cited

U.S. PATENT DOCUMENTS 3,234,106  2/1966  Hink et al. ........................... 424/101

FOREIGN PATENT DOCUMENTS 1,347,029  11/1963  France.

OTHER PUBLICATIONS

The Journal of Biological Chemistry, vol. 246, No. 14, issue of Jul. 25, 1971, pp. 4641–4647.

Science, vol. 170, No. 3959, Nov. 13, 1970, pp. 1095 & 1096.
Chemical Abstracts, vol. 80, p. 148, which includes references to Aichi Ika Daigaku Igakukai Zasshi, (1973), 1(4), pp. 247–262.
Rickli et al., Biochim. Biophys. Acta, 250 (1971), pp. 447–451.
Rickli et al., Biochim. Biophys. Acta, 295 (1973), pp. 381–384.
Wallen et al., Biochim. Biophys. Acta., 221 (1970), pp. 20–30.
Claeys et al., Biochimica et Biophysica Acta. 342 (1974), pp. 351–359.

*Primary Examiner*—Sam Rosen
*Attorney, Agent, or Firm*—Weiser, Stapler & Spivak

[57] ABSTRACT

The placental pulps notably of human origin are separated from the placental blood, which is removed, and the pulps are macerated in a solution at a pH comprised between 5 and 10, e.g. isotonic NaCl solution, preferably at neutral pH, in the presence of an amino-acid inhibitor of plasminogen activation, at a molar concentration comprised between about 0.001 and 0.1 M, preferably of the order of 0.035 M. The pulps are removed and the solution containing the compounds of the plasminogen type is recovered. Preferred inhibitors are L-lysine, epsilon aminocaproic acid, and trans-4 aminomethyl cyclohexane carboxylic acid.

55 Claims, No Drawings

COMPOUNDS OF THE PLASMINOGEN TYPE AND METHOD FOR OBTAINING SUCH COMPOUNDS FROM PLACENTAL PULPS

The invention relates to active compounds of the plasminogen type, preferably of human origin, to medicaments containing these compounds and to a method for the extraction of these active compounds from placental pulps.

Plasminogen, also called profibrinolysin is a protein which exists normally in plasma and which can be converted into plasmin (or fibrinolysin) by the action of an activator, such as a kinase. Taking into account the property possessed by plasmin of inducing rapid solution of blood clots, it has already been proposed to use plasminogen as an active principle in thrombolytic medicaments.

Various methods of extracting plasminogen have already been proposed. Preferably, especially when its use is contemplated as an active principle in thrombolytic medicaments, this plasminogen must be of human origin. The sources of plasminogen to be taken into consideration therefore are essentially constituted by blood plasma and, although to a lesser degree until now, human placentas.

Plasma appears in fact to constitute basically the raw material of choice for plasminogen. The latter is in fact present in the dissolved state in plasma with other proteins, from which it can be separated in relatively easy manner, due to fractionating techniques applying notably techniques of fractional precipitation.

For example, it has been proposed to use the known property of certain plasminogen inhibitors to increase the solubility of the latter in a slightly acidified medium, notably at a pH comprised between 5.3 and 6, to produce precipitation of a certain amount of proteins which accompany it in plasmatic preparations.

Since plasmas are generally reserved for other uses, it has become interesting to turn to human placentas, more particularly to placental blood, as possible sources of plasminogen. It is however acknowledged that the techniques of extraction of plasminogen from plasma, which have been studied in laboratory, are not applicable as such to the extraction of plasminogen from placental blood and this is doubtless by reason of the different nature of the proteins, and lipids which accompany the plasminogen in placental blood. The latter contains in particular high proportions of plasmin. The separation of plasminogen from plasmin is difficult to accomplish.

It should also be noted that all known methods for extracting plasminogen from human placental blood call upon acid extraction media, notably for the purpose of preventing activation of the plasminogen into plasmin under the effect of the natural activators which accompany it in this raw material.

It will be recalled however that the pH of extraction media is not without effect on the physical properties of the plasminogens obtained. In particular, acidification of the medium, notably at pH values less than 5-6, involves alteration of certain physical properties of the plasminogen. In practice, the stability and the solubility in a neutral medium of a plasminogen obtained in an acid medium are very much reduced with respect to those of the native plasminogen.

The solubility of the plasminogen obtained under these conditions can certainly be somewhat improved, in a moreover reversible manner, by the addition to the medium of certain inhibitors of plasminogen inactivation or by the modification of the ionic force of the medium, notably by the introduction into the latter of salts in certain proportions; but the presence of these inhibitors or of these salts in the solutions obtained makes difficult, if not impossible, the use of such solutions for the constitution of medicaments, especially where they relate to medicaments administered by the parenteral route. Any attempt at prior separation of these inhibitors or salts would involve the reprecipitation of the plasminogen from these solutions.

There has also been described, notably in French Patent No. 1,347,029, a method of extraction, this time from frozen and pulped complete placentas, of an agent possessing plasminogen properties, notably in that it is suited to rendering bovine blood sensitive to the action of streptokinase. This is however still a method of extraction in an acid medium. A product is obtained which can be solubilised to a certain extent, especially when recourse is had to the expedients mentioned above. It contains however notable proportions of proteins, especially of plasmin. It has been observed besides that the presence of these other proteins plays a non-negligible role in the solubilisation of the product, since any attempt at additional separation of proteins is accompanied by precipitation of the fraction enriched in plasminogen activity.

It is an object of the invention to overcome these difficulties, notably to provide a product containing compounds of the plasminogen type, having a high degree of purity, substantially or even entirely free of plasmin, completely soluble in a neutral medium, even in the abscence of inhibitors of activation of the plasminogen or of mineral salts, as well as a method for the extraction of this product, from placentas, in the absence of any intermediate acidification step.

The invention rests on the discovery that it is possible to extract compounds of the plasminogen type retained, even fixed in placental pulps, after the elimination of the placental blood, by causing these pulps to be macerated at a neutral pH in the presence of an inhibitor of the activation of the plasminogen.

In other words, the method according to the invention is characterised in that the placental pulps are separated from the placental blood, which is removed, and in that the pulps are macerated in the midst of a solution at a pH comprised between 5 and 10, preferably at neutral pH, in the presence of an inhibitor of the activation of plasminogen, notably of an ε-amino-acid, and that the pulps are removed. There is then obtained, notably after separation of the inhibitor, a solution of a crude product containing the abovementioned compounds of the plasminogen type, which are sometimes denoted below as a whole, for convenience of language, by the expression "placental plasminogen".

It is interesting to note that the mode of retention of the plasminogen on the placental pulps appears to a certain extent as the mode of fixing an enzyme on a substrate of affinity chromatography, the enzyme being then eluted by means of a solution of a specific inhibitor of this enzyme.

This extraction may be effected in the absence of any mineral salts, hence in water. It is noted however that it is advantageous to work with physiological sera, preferably isotonic chloride solutions, notably with a 9/1000 sodium chloride solution. It is observed in fact that the extraction of the foreign proteins is then, with these solutions, reduced to a minimum, whence the possibility of obtaining, after this extraction operation, of fractions very enriched in compounds or substances having the characteristics of placental plasminogen and capable of being activated into plasmin. Reference will be made in the following to "the potential plasminic acitivity" of these compounds or substances.

An important additional advantage of the method according to the invention resides in the fact that it achieves effective protection of the placental plasminogen with respect to its activators at physiological pH, during the extraction operation itself, that is to say at the time when it is normally most subject to activation.

In a preferred embodiment of the method according to the invention, the molar concentration of the inhibitor used is generally comprised between about 0.001 and 0.1 M, preferably in the vicinity of the value 0.035 M.

Plasminogen activation inhibitors which are particularly advantageous in the application of the method according to the invention are L-lysine of the formula:

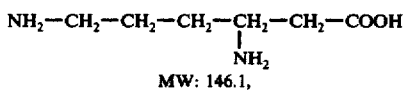

epsilon aminocaproic acid (AεAC) of the formula:

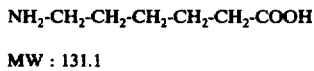

or trans-4 aminomethyl cyclohexane carboxylic acid (AMCHA) of the formula:

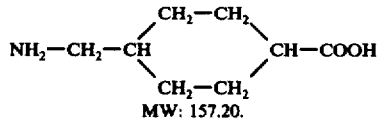

Hence there is obtained, directly after the separation of the inhibitors from the maceration bath, a solution of plasminogen under physiological conditions of salinity and pH.

The same operations of maceration, however, in the absence of a plasminogen inhibitor, only permit the extraction of a much smaller, even negligible amount, of placental plasminogen, as will emerge from the examples described below.

It must be stressed that the placental plasminogen contained in the solutions obtained is soluble in physiological media, all the operations of separation and of maceration having been carried out at a pH compatible with the preservation of this state.

It is then possible to proceed with the separation of the plasminogen inhibitor by resorting to conventional methods, whose application will often be all the more facilitated as the molecular weights of the compounds of the plasminogen type on the one hand, and of the inhibitor on the other hand, are extremely different. By way of example, separation technics will be mentioned which apply fractional precipitations by means of agents not altering the enzymatic properties of the compounds of the plasminogen type. The preferred agent is ammonium sulfate, particularly cheap, giving rise to highly concentrated aqueous solutions. It is possible of course to use any other salt useful for the same purpose, for example ammonium chloride, magnesium sulfate of sodium sulfate. Recourse may also be had to other fractional precipitation agents, such as an alcohol, the plasminogen then being separable in the form of a precipitate from the aminoacids which remain in solution.

It is also possible to resort to separation methods by physical means, notably by dialysis or by filtration on a molecular sieve, for example on a gel known commercially as "SEPHADEX."

It is also possible to use ion exchange operations in a neutral or very slightly alkaline medium, for example at pH 8, the inhibitor being elutable while the plasminogen remains absorbed on the resin. It is self-evident that the various methods mentioned are only for the purpose of illustrating the great facility with which the compounds of the plasminogen type can be recovered from the maceration solutions.

The crude solution of placental plasminogen contains, besides the placental plasminogen itself, impurities, the major portion of which (notably 90 to 95%) is of proteinic nature.

The separation of these proteinic impurities can be carried out in any manner known per se preferably however, the separation is performed by a fractional precipitation of a solution of the crude plasminogen and of a large part of the proteinic impurities, notably by resorting to salts such as those which have been identified above, by redissolving the precipitate containing the placental plasminogen in an aqueous solution and by subjecting the latter to dialysis, by subjecting the dialysate to an additional purification by resorting to affinity chromatography on a substrate on which the inhibitor of the plasminogen activation, preferably lysine, is fixed by covalent bonds, by eluting the placental plasminogen retained on the substrate by a solution of inhibitor of the plasminogen activation, preferably epsilon aminocaproic acid, and by finally subjecting the eluate to an additional dialysis for removing the inhibitor, all the preceding operations being carried out at pH values above 5.

The potential plasminic activity of these placental plasminogens is extremely high as is witnessed by their pharmacological properties which are indicated below.

Analytical study of the placental plasminogen has shown that it comprises high proportions of peptides, called below "preactivated plasminogens", resulting from the loss by the whole or "native" plasminogen of peptidic fragments comprising a number of aminoacids, of the order of 68, having a molecular weight of the order of 7000–8000, from the side of the end of the peptidic chain which forms the native plasminogen, which is terminated by an aminoacid with a free-$NH_2$ group, principally glutamic acids (the other extremity of the plasminogen peptidic chain being principally asparagine, the carboxy group of which is free according to ROBBINS et al, J. Biol. Chem. 242, 2333–2342, 1967). The remaining proportions of compounds with potential plasminic activity contained in the placental plasminogen are, apart from inert impurities, native plasminogen.

Among preactivated plasminogens, the predominant presence of peptidic chains having a terminal aminoacid with a free-$NH_2$ group, constituted by methionine, is noted. In the following, this preactivated plasminogen is denoted by the expression "methionine-plasminogen". Fairly high proportions of a preactivated plasminogen will also be noted having a terminal aminoacid with a free $NH_2$ group constituted by valine, denoted in the following by the expression "valine-plasminogen."

The invention therefore relates to compositions of the plasminogen type containing a large proportion, at least about 40%, of methionine-plasminogen.

The placental plasminogen, according to the invention, contains, in particular, of the order of 40 to 60% by weight of methionine-plasminogen.

In particular, the invention relates to compositions containing compounds with potential plasminic activity, containing:
- about 40 to about 60% by weight of methionine-plasminogen,
- from about 10 to about 20% by weight of valineplasminogen,
- from about 20 to about 50% by weight of native plasminogen.

Taking into account that the molecular weight of native plasminogen is situated at 90,000 ± 5,000, those of the preactivated plasminogens are of the order of 83,000 ± 5,000.

More particularly again, the invention relates to placental plasminogens of the type which has been described, having a degree of purity which can reach, even exceed 95%, the remainder being proteins or inert impurities, these purified placental plasminogens being obtained from the abovesaid crude plasminogens by conventional purification operations for the plasminogen, for example of the type defined in the preferred general operational method described below.

The invention relates also to medicaments in which the abovementioned placental plasminogens are associated with an injectable sterile liquid vehicle or a sterile perfusion liquid.

In a general way, recourse will advantageously be had to the following general mode of operation, applicable notably to human plasmas. Where reference is made in the following to the extraction of plasminogen, it must naturally be understood as "placental plasminogen" as defined above.

The placentas, frozen delivery, are stored at $-20°$ C. They are pulped mechanically in the frozen condition.

The pulp obtained is then defrosted by contact with a water bath at a temperature of $+30°$ to $+40°$ C., with mechanical stirring. The defrosting is completed when the pulps reach a temperature above $1°$ C., preferably $4°$ C.

The fluid mass obtained is centrifuged at 2,500 rpm, so as to remove the placental blood which contains little plasminogen, but a large amount of proteins and plasmin.

The drained pulps are subjected to maceration for three hours in a bath of isotonic chloride solution, at a temperature comprised between $0°$ and $+20°$ C., preferably $+4°$ C.

This bath contains a low molar concentration of one of the inhibitors described above, in a molar concentration higher than 0.001 M, preferably close to 0.035 M. No correction is applied to the pH of the whole which thus remains at 7.2.

The maceration time having elapsed, the whole is centrifuged at 2500 rpm, so as to separate the pulps from the extraction bath.

In this way a liter of extraction liquid per kilo of placenta used is obtained, containing 120 CAU (caseinolytic units) and corresponding to 15 mg of pure plasminogen. The titration method used is that known under the name "CASEINOLYTIC METHOD."

The plasminogen contained in the solutions obtained may be recovered and purified by resorting to known methods. Advantageously, there follows fractional precipitation of the proteins and of the plasminogen contained in the solution by ammonium sulfate. Addition to the solution of an amount of ammonium sulfate corresponding to 20% of saturation of the solution in this salt (it being understood that a solution is 100% saturated when it contains 540 g of ammonium sulfate per liter) enables precipitation of a part of the proteins from the solution, increasing the percentage saturation in ammonium sulfate upto 40% enabling precipitation of the plasminogen. These operations are effected at a pH comprised between 5.5 and 9.5, preferably at neutral pH. The precipitated plasminogen is then redissolved in a buffer solution, the pH of which is between about 6.5 and about 9.5, enabling additional purification by dialysis, notably for removing the residual ammonium sulfate. The dialysate is then subjected to a final purification operation by affinity chromatography, for example in the presence of the disodium salt of ethylene-diaminetetracetic acid, on a column containing a substrate, such as agar-agar gel on which an inhibitor of the plasminogen activation, preferably lysine is fixed by a covalent bond, the plasminogen then being recovered by elution by means of a buffer containing epsilon aminocaproic acid. As necessary, the eluate can again undergo an additional purification by dialysis, notably for separating the inhibitor.

In a general way, these operations can be carried out under the conditions which have been described in the litterature, it being understood that the operational modes selected will be those which permit working in all circumstances, at pH higher than 5.

There is thus obtained a product having a high plasminogen activity, whose content of plasminogen can be higher than 4 CAU/mg and a content of plasmin less than 0.04 CAU/mg.

It is understood that in the foregoing the plasminogen contents are expressed after activation by urokinase and the plasmin contents represent spontaneous plasmin (present before the activation).

The placental plasminogen obtainable by the method according to the invention is characterised in that, after purification:
- it is monodispersed to electrophoresis,
- it is soluble in water, in isotonic chloride solutions and in buffers of current compositions at neutral pH,
- it is stable at neutral pH, it is apyrogenic at doses of 10 CAU/kg of rabbit,
- it is devoid of toxicity with respect to the mouse at doses of 10 CAU per mouse.

The effectiveness of the method according to the invention is established by comparison of the results obtained by application of the operations which are described in Example 1 below, on the one hand in the presence, and on the other hand in the absence, of an inhibitor of plasminogen activation.

EXAMPLE 1

Extractive effect of plasminogen activation inhibitors 1500 g of human placenta, frozen to $-20°$ C., are pulped in a STEPHAN type grinder.

The mass obtained is thawed by manual stirring in a stainless steel container in contact with a water bath at 40° C. The defrosting lasts 40 minutes. The final temperature of the mass is +6° C.

The placental blood is then separated by centrifugation of the defrosted mass, in a cup centrifuge, cooled to +4° C. at 2,500 rpm for one hour.

740 ml of placental blood (790 g) containing 290 g of proteins and an amount of plasminogen less than 70 CAU, are obtained.

The pulp obtained (700 g) is divided into three equal parts of 233 g : part No. 1, part No. 2 and part No. 3. These three parts are treated simultaneously under the same conditions, with the exception of the composition of the maceration bath, and in the following manner:

Part No. 1 is macerated in 500 ml of a bath composed as follows:
distilled water: 500 ml
NaCl: 4.5 g
phenol (bacteriostatic agent): 0.5 g
bath temperature: +5° C.;

Part No. 2 is treated in the same manner in a bath composed of:
distilled water: 500 ml
NaCl: 4.5 g
phenol: 0.5 g
epsilon aminocaprioc acid 2.5 g viz.0.038 M
bath temperature +5° C.
finally, Part No. 3 is macerated in:
distilled water: 500 ml
NaCl: 4.5 g
phenol: 0.5 g
trans-4-aminomethylcyclohexane carboxylic acid (AMCHA): 2.5 g viz.0.032M
bath temperature: +5° C.

These three macerations are carried out in parallel in three beakers of a liter, at +4° C., with intermittent manual stirring for three hours. The pH is left as it is and was 7.2 in the three cases.

The time of maceration having elapsed, the three suspensions were centrifuged simultaneously in centrifuges cooled to +4° C. for one hour at 2500 rpm.

The pulps were separated and the following volumes of supernatant liquid obtained:
Volume 1: 500 ml
Volume 2: 500 ml
Volume 3: 505 ml The three supernatant liquids were brought to 40% of saturation in ammonium sulfate by the addition of 240 g/l of this crystalline salt, with mechanical stirring. The stirring was continued in the three cases, for 20 minutes after the end of addition of the salt. The pH left as it was registered 6.9 in the three cases.

The three solutions were centrifuged simultaneously in centrifuges cooled to +4° C., at 2500 rpm, for 1 1/2 hours. The three supernatant liquids were separated, and the three precipitates which were collected weighed:
precipitate 1: 23 g
precipitate 2: 23.2 g
precipitate 3: 24 g These three precipitates were composed approximately of 90% mother liquors and 10% proteins.

The three precipitates were dissolved respectively in 50 ml of 0.1 M, pH 7.5, phosphate buffer, then dialysed for three hours against running demineralized cold water. A final dialysis was carried out for 15 hours against 40 liters of 0.01 M, pH 7.5, phosphate buffer at +4° C.

The three dialysates obtained had the following characteristics:
Dialysate 1: volume: 80 ml; pH 7.5; conductivity: 950 $\mu$mhos
Dialysate 2: volume: 82 ml; pH 7.5; conductivity: 940 $\mu$mhos
Dialysate 3: volume: 94 ml; pH 7.5; conductivity: 980 $\mu$mhos.

Their plasminogen activities were as follows:
Dialysate 1: 0.16 CAU/ml × 80 ml = 12.8 CAU
Dialysate 2: 0.85 CAU/ml × 82 ml = 69.5 CAU
Dialysate 3 : 0.75 CAU/ml × 94 ml = 70.5 CAU The examination of the latter results established the quality of the extraction results obtainable by the method according to the invention.

In example 2 below is described the extraction step on a larger scale, of a placental plasminogen from a placenta.

EXAMPLE 2

A: Extraction of the Plasminogen 500 kg of human placenta frozen to −20° C. were finally pulped by means of a PALMANN type grinder.

The mass obtained was defrosted by stirring in a WERNER type mixer in the double envelope of which circulation of water at +40° C. was established.

Defrosting lasted 2 h. 30 and the final temperature of the mass was +4° C.

The placental blood was then separated by centrifugation of the defrosted mass in a ROUSSELET type centrifuge, at 2500 rpm., in five passes of 15 minutes.

238 kg of pulps and 260 kg of blood were thus obtained.

The pulps were thrown into a maceration bath of the following composition:
physiologic serum: 500 liters
epsilon aminocaproic acid: 2500 g (0.038 M)
phenol (bacteriostatic agent): 500 g (1%°)
bath temperature: 4° C.

The whole was stirred for three hours at +4° C. The pH of the medium was not modified: it was 7.2.

The extraction liquid was then separated from the pulps by centrifugation in a ROUSSELET type centrifuge, at 2500 rpm., in five passes of 15 minutes.

The extraction liquid had then a temperature of 8° C., a pH of 7.2, and a volume of 510 liters.

B: Purification of the Plasminogen

The purification of the plasminogen contained in the solution obtained can be effected for example by operating in the following manner.

The purification method used is a modification of the method known by the name of affinity chromatography.

The extraction liquid is first filtered to clarity in the presence of a filtration adjuvant, such as that known commercially as SOLKA FLOC BW 20 (clearfiltration) or centrifuged at high speed, after the addition of an amount of ammonium sulfate corresponding to 20% of saturation; this clarification filtration or centrifugation has the object of removing the fine particles of pulp which could remain in the solution.

The extraction liquid was then brought to 40% of saturation in ammonium sulfate, in order to precipitate the plasminogen.

The clearfiltration(or centrifugation) and the precipitation were carried out at a pH comprised between 5.5 and 9.5, preferably 7 (pH obtained naturally without the addition of acid or base to the medium).

The precipitate obtained was redissolved in a solution in cold demineralised water of one of the inhibitors described above (molarity comprised between 0.001 M and 0.05 M), so as to obtain a conductivity less than 20,000 micromhos, preferably 12,000 micromhos.

The pH is then adjusted to a value comprised between 5.2 and 7, preferably 5.5.

By filtration, the filtration adjuvant previously added is removed as well as inactive impurities.

The filtrate obtained is adjusted to a pH comprised between 5.5 and 9, preferably 7.2, then diluted once by the addition of its own volume of cold mineralized water.

Active material from the solution obtained is then precipitated by bringing the latter to 40% saturation in ammonium sulfate.

The precipitate is collected by centrifugation.

It is dissolved in a phosphate buffer of 0.1 to 0.5 M, preferably 0.3 M, pH 6.5 to 9.5, preferably 7.5, then dialysed 7 to 8 hours against cold demineralized water, so as to obtain a conductivity situated between 6000 and 10000 micromhos.

The dialysate is then centrifuged, or clearfiltered, to remove the insoluble substances which have appeared in the course of dialysis.

To the clearfiltered or centrifuged solution, there is added 1% (weight volume) of ethylene diamine tetracetate acid disodium salt (EDTA) and its pH is adjusted to a value comprised between 6 and 9, preferably 7.5, by means of soda and orthophosphoric acid.

The solution is then poured on to a column containing agar-agar gel, on which the lysine is fixed by covalent bond, and preequilibrated with a phosphate buffer of 0.05 to 0.4 molarity, preferably 0.15 M, pH 6 to 9, preferably 7.5 (buffer No. 1). When all the solution has passed over the column the latter is rinsed with the buffer No. 1 until the absence of proteins in the effluent. The rinsing buffer is then displaced by phosphate buffer of molarity 0.05 to 0.4 M, preferably 0.1 M, pH 6 to 9, preferably 7.5 (buffer No. 2). The column is then eluted by buffer No. 2 containing 0.01 M to 0.5 M epsilon aminocaproic acid, preferably 0.2 M.

The eluate is collected: it contains almost all the plasminogen extracted. It is then dialysed 24 h against a buffer of low molarity, pH 6 to 9, preferably phosphate buffer 0.01 M, pH 7.5, then lyophilized.

There were thus obtained between 100 and 120 CAU of plasminogen per kilo of placenta used.

Starting from the above-indicated crude solution 5.2 g of lyophilized powder were thus obtained having the following characteristics:
content of plasminogen: 4.4 CAU/mg
plasmin content: 0.04 CAU/mg
protein content: 52% (48% remaining being constituted by phosphates).

This powder is characterised by a complete solubility at pH of the order of 7 in distilled water, isotonic chloride solutions and buffers of current composition, and in a general way have all the characteristics which have been mentioned above.

Generally, one may therefore consider that the product of plasminogenic type extracted from placental pulps has a content of plasminogen higher than 4 CAU/mg and a content of plasmin less than 0.04 CAU/mg.

The placental plasminogen thus obtained has high pharmacological activity and excellent therapeutic properties.

Pharmacological experiments on plasminogen by applying the technique described by R. Courbier and Coll., Ann. Chir., 1963, 17, No. 5-6, pp. 331-338, in dogs in which experimental acute arterial thrombases have been caused, shows that the plasminogen induces a rapid reduction in the size of clots and even, in the majority of cases, complete lysis.

In this respect it is interesting to observe that an amount of the product according to the invention, comprising 13 mg of proteins and titrating 100 CAU, has, in the abovementioned pharmacological experiments, an activity substantially similar to that obtained with an amount of the product, obtained according to French Patent 1,347,029, containing 240 mg of proteins.

In a general way, the placental plasminogen is applied to the treatment of deficiencies of the fibrinolytic function.

The use of human placental plasminogen is advantageous, notably in the case of the following clinical indications:

(a) acute respiratory distress of the newly born and premature infants in which complete or partial deficiency of plasminogen is present, which syndrome is generally connected with deposition of fibrin at the level of the pulmonary alveoli;

(b) emboli and veinous thromboses, notably in those patients whose consumption of plasminogen is greater than the production at the level of the liver, the administration of plasminogen then being recommended to prepare the patients concerned for thrombolytic treatment by a medicament such as streptokinase or urokinase;

(c) essentially cerebral micro-embolisms;

(d) localized and disseminated, acute, sub-acute and chronic intravascular coagulations, with a tendency to spread due to plasminogen deficiency.

Purely by way of indication, the administration of the placental plasminogen can be effected by continuous veinous perfusion, at the rate of 1,000 to 1,200 CAU spread over a period of 24 to 36 hours, or by slow intraveinous injection (for a man of average weight 60 kg).

For infants, recourse is had to doses of 200 CAU every six hours, administered in slow perfusion, in a 9% isotonic chloride solution, buffered to pH 7.4 for 24 hours.

For these forms of administration, recourse is had to solution of plasmogen in a pharmaceutically acceptable vehicle, notably a physiologic serum, preferably glucose.

We claim:

1. A method for the preparation of an active plasminogen compound capable of activation to plasmin which comprises mechanically reducing frozen placentas to placental pulps, defrosing the resulting pulps, thereby obtaining a fluid mass of placental liquid and solids, separating from the mass of liquid and solids the liquid which contains the fluid placental blood, which liquid contains proteins and plasmins and recovering the placental solids including the pulps, macerating said pulps at a pH between about 5 and about 10 in an aqueous solution of an inhibitor of plasminogen activation to plasmin, removing the pulps, collecting the liquid solution containing the plasminogen compounds, separating said inhibitor of plasminogen activation and recovering the solution of the plasminogen dissolved therein.

2. Method according to claim 1, wherein said placentas are of human origin.

3. Method according to claim 1, wherein said maceration is conducted at neutral pH.

4. Method according to claim 1, wherein the maceration is effected in an isotonic chloride solution of sodium chloride.

5. Method according to claim 1, wherein the inhibitor amino-acid is used at a molar concentraction comprised between about 0.001 and 0.1 M.

6. Method according to claim 1, wherein the inhibitor concentration is of the order of 0.035 M.

7. Method according to claim 1, including the step of separating the product of the plasminogen type from said solution of plasminogen.

8. Method according to claim 1, including separating said product of the plasminogen type by fractional precipitation.

9. Method according to claim 8, wherein said fractional precipitation is done with ammonium sulfate.

10. The method of claim 1 which comprises:
subjecting the solution containing the plasminogen dissolved therein to fractional precipitation, thereby separating the proteinic impurities,
recovering the precipitate in an aqueous solution,
subjecting the aqueous solution containing the dissolved precipitate of plasminogen to dialysis,
recovering the dialyate,
subjecting it to affinity chromotography on a substrate on which there is fixed an inhibitor of plasminogen activation,
eluting the plasminogen retained on the substrate and redialysing the eluate, thereby obtaining a solution of purified plasminogen free of inhibitor of plasminogen activation, all the above-recited steps being carried out at a pH above about 5.0.

11. The method of claim 10 wherein inhibitor of plasminogen activity which is fixed on the substrate is lysine.

12. The method of claim 1 wherein the separation of pulp solids is carried out on the defrosted cold mass at low temperature.

13. composition having polasminogen activity capable of activation to plasmin which composition comprises native plasminogen and preactivated plasminogen said preactivated plasminogen having a molecular weight which is of about 7000 to 8000 less than the molecular weight of the native plasminogen, said composition being substantially free of plasmin and soluble in distilled water.

14. Composition according to claim 13, containing at least about 40% by weight of methionin plasminogen.

15. Composition according to claim 13, containing between about 40% and about 60% by weight of methionin plasminogen.

16. Composition according to claim 13, containing:
from about 40 to about 60% by weight of methionin-plasminogen,
from about 10 to about 20% by weight of valine-plasimogen,
from about 20 to about 50% by weight of native plasminogen.

17. Composition according to claim 13, characterised in that:
it is monodispersed to electrophoresis;
it is soluble in water, in isotonic chloride solutions and in buffers of current compositions at neutral pH,
it is stable at a neutral pH, it is apyrogenic at doses of 10 CAU/kg of rabbit;
it is free of toxicity with respect to the mouse at doses of 10 CAU per mouse.

18. Composition according to claim 13, having a plasminogen content higher than 4 CAU/mg and a plasmin content less than 0.04 CAU/mg.

19. Medicament containing, by way of active principle, a composition according to claim 13, associated with a physiologically acceptable parenteral vehicle.

20. Medicament according to claim 19, in the form of an injectable solution or of a perfusion solution, in which the vehicle is an isotonic, sterile solution.

21. Method for treating deficiencies of the fibrinolytic function, in a warm-blooded animal, comprising administering the composition according to claim 13, by the injectable route or by perfusion.

22. A method for the preparation of an active, purified placental plasminogen compound capable of activation to plasmin which comprises macerating at a pH between about 5 and about 10 placental pulps substantially free of placental blood in an aqueous solution of an inhibitor of plasminogen activation to plasmin, removing the pulps, collecting the solution containing the plasminogen compound, separating the inhibitor of plasminogen activation and recovering the solution of the plasminogen compound dissolved therein.

23. The process of claim 22 wherein the pH is in the range of about 7 to 10.

24. The process of claim 22 which comprises native plasminogen and preactivated plasminogens, these having a molecular weight of about 7000 to 8000 less than that of the native plasminogen and said compound being substantially free of plasmin and further purifying by separating out the proteins.

25. The process of claim 22 wherein the pH is in the range of about 5 to 7.

26. The method of claim 22 in which the plasminogen is soluble in distilled water.

27. The method of claim 22 wherein the inhibitor is an amino-acid.

28. The method of claim 27 wherein the amino acid is an epsilon amino-acid---.

29. The method of claim 22 wherein the placental pulps are human placental pulps.

30. The method of claim 22 wherein the pH is about neutral.

31. The method of claim 22 wherein the maceration is carried out in an isotonic chloride solution.

32. The method of claim 27 wherein the inhibitor is L-lysin.

33. The method of claim 27 wherein the inhibitor is epsilon aminocaproic acid.

34. The method of claim 27 wherein the inhibitor is trans-4-aminoethyl cyclohexane carboxylic acid.

35. The method of claim 27 wherein the concentration of the inhibitor is a molar concentration in the range of about 0.001 and 0.1 M.

36. The method of claim 22 wherein the solution containing the plasminogen and the inhibitor is subjected to fraction precipitation, thereby separating the plasminogen from the solution of amino acids.

37. The method of claim 22 which comprises after recovery of the plasminogen further purifying it by separating the proteinic impurities.

38. A composition of placental plasminogen having plasminogen activity capable of activation to plasmin which composition comprises in addition to native plasminogen, preactivated plasminogen having a molecular weight by about 7000 to 8000 lower than the molecular weight of the native plasminogen, in a proportion of at least 40% by weight with respect to the total amount of said plasminogen, which composition is stable, is substantially free of plasmin and is soluble in distilled water.

39. The lyophilsate of the composition of claim 38.

40. The composition of claim 38 of a degree of purity of about at least 95%.

41. The placental-plasminogen of claim 38 wherein the plasmimogen is at least 40% by weight of methionin-plasminogen.

42. The placental-plasminogen of claim 38 wherein the plasminogen is about 40 to about 60% by weight of methionin-plasminogen.

43. The placental plasminogen of claim 38 wherein the plasminogen is at least from about 40 to about 60% by weight of methionin-plasminogen; from about 10 to about 20% by weight of valine-plasminogen and from about 20 to 50% by weight of native plasminogen.

44. The placental-plasminogen of claim 38 which is human placental-plasminogen.

45. The placental-plasminogen of claim 38 which is water-soluble, soluble in isotonic chloride solution and soluble and stable in buffered solution at neutral pH, and is apyrogenic.

46. A solution of the composition of 38.

47. The composition of claim 38 wherein the native plasminogen has a molecular weight of about 90,000 ± 5,000 and the preactivated plasminogen has a molecular weight of about 83,000 ± 5,000.

48. The composition of claim 38 which has a plasminogen content higher than 4 CAU/mg and a plasmin content less than 0.04 CAU/mg.

49. A composition of placental plasminogen having plasminogen activity capable of activation to plasmin, which composition comprises native plasminogen having a molecular weight of about 90,000 ± 5,000 and preactivated plasminogen is a proportion of at least 40% by weight with respect to the total amount of the plasminogen said preactivated having a molecular weight of 83,000 ± 5,000, which composition is substantially free of plasmin and is soluble in distilled water.

50. A composition of placental plasminogen having plasminogen activity capable of activation to plasmin which composition comprises in addition to native plasminogen whose terminal amino-acid is glutamic acid which acid has a free amino group, another plasminogen which plasminogen has a lower molecular weight than the native plasminogen said plasminogen being present in a proportion of at least 40% by weight with respect to the total of plasminogen, said other plasminogen differing from native plasminogen by the absence of a peptidic fragment including said terminal amino-acid, the terminal amino-acid of said other plasminogen being methionine with a free amino group, which composition is stable, is substantially free of plasmin and is soluble in distilled water.

51. The composition of claim 50 which comprises yet another plasminogen which differs from native plasminogen by the absence of peptidic fragment including said amino acid, the terminal amino-acid of said another plasminogen being valine with a free amino group.

52. The composition of claim 51 wherein the proportion of plasminogen having a methionine terminal group is about 40 to about 60% by weight, and the plasminogen having a valine terminal group is about 10 to about 20% by weight.

53. A medicament of placental plasminogen comprising in association, a physiologically acceptable parenteral vehicle and the composition of claim 50.

54. A medicament of placental plasminogen comprising in association, a physiologically acceptable parenteral vehicle and the composition of claim 51.

55. A medicament of placental plasminogen comprising in association, a physiologically acceptable parenteral vehicle and the composition of claim 52.

* * * * *